(12) United States Patent
Göbel

(10) Patent No.: US 11,376,381 B2
(45) Date of Patent: Jul. 5, 2022

(54) DEVICE FOR A DYNAMICALLY SEALING OCCLUSION OR A SPACE-FILLING TAMPONADE OF A HOLLOW ORGAN

(71) Applicant: Creative Balloons GmbH, Waghäusel (DE)

(72) Inventor: Fred Göbel, Wilhelmsfeld (DE)

(73) Assignee: Creative Balloons GmbH, Waghäusel (DE)

( * ) Notice: Subject to any disclaimer, the term of this patent is extended or adjusted under 35 U.S.C. 154(b) by 646 days.

(21) Appl. No.: 15/777,439

(22) PCT Filed: Nov. 18, 2016

(86) PCT No.: PCT/IB2016/001643
§ 371 (c)(1),
(2) Date: May 18, 2018

(87) PCT Pub. No.: WO2017/085540
PCT Pub. Date: May 26, 2017

(65) Prior Publication Data
US 2018/0333552 A1   Nov. 22, 2018

Related U.S. Application Data

(63) Continuation-in-part of application No. PCT/IB2015/002309, filed on Dec. 4, 2015.

(30) Foreign Application Priority Data

Nov. 18, 2015 (DE) ................. 10 2015 014 824.9
Dec. 4, 2015 (WO) ................. PCT/IB2015/002309

(51) Int. Cl.
*A61M 16/04* (2006.01)
*A61M 29/02* (2006.01)
*A61M 25/10* (2013.01)

(52) U.S. Cl.
CPC ...... *A61M 16/044* (2013.01); *A61M 16/0447* (2014.02); *A61M 29/02* (2013.01);
(Continued)

(58) Field of Classification Search
CPC ...... A61M 16/00; A61M 16/003–0012; A61M 16/04; A61M 16/0402–0486; A61M 2016/0015–0042
See application file for complete search history.

(56) References Cited

U.S. PATENT DOCUMENTS 3,794,043 A   2/1974   McGinnis
3,848,605 A   11/1974  Harautuneian et al.
(Continued)

FOREIGN PATENT DOCUMENTS

DE   3712502 A1   10/1988
DE   3742710      7/1989
(Continued)

OTHER PUBLICATIONS

Badenhorst, Changes in Tracheal Cuff Pressure in Respiratory Support, Critical Care Medicine, vol. 15, No. 4, 1987, pp. 300-302.
(Continued)

*Primary Examiner* — Victoria Murphy
*Assistant Examiner* — Ned T Heffner
(74) *Attorney, Agent, or Firm* — Pandiscio & Pandiscio

(57) ABSTRACT

The invention is directed to a device for the sealing occlusion and/or for the space-filling tamponade of hollow organs or other cavities in the human body, comprising a preferably fully and residually formed balloon (2) which applies a sealing pressure that is as constant as possible to the wall of the organ to be occluded or tamponaded. The device comprises an isobarically acting regulator (3) for the filling pressure within the interior of the balloon, the regulator having a volume reservoir (3) situated extracorporeally
(Continued)

outside of the body, and a feed line (6) for communicatively connecting the extracorporeal volume reservoir of the regulator to the interior of the balloon. The connecting feed line between the balloon and the regulator has a flow-directing one-way valve (26) that prevents backflow from the balloon to the volume reservoir of the regulator, while a nonflow-directing throttle element (27) is provided which allows a slow volume compensation between the balloon and the volume reservoir.

23 Claims, 8 Drawing Sheets

(52) U.S. Cl.
CPC ............... *A61M 25/10186* (2013.11); *A61M 2025/1004* (2013.01); *A61M 2025/1061* (2013.01)

(56) References Cited

U.S. PATENT DOCUMENTS

| | | | |
|---|---|---|---|
| 4,159,722 A | 7/1979 | Walker | |
| 4,285,340 A | 8/1981 | Gezari et al. | |
| 4,501,273 A | 2/1985 | McGinnis | |
| 4,649,914 A * | 3/1987 | Kowalewski | A61M 16/044 |
| | | | 128/207.15 |
| 4,762,129 A | 8/1988 | Bonzel | |
| 4,770,170 A | 9/1988 | Sato et al. | |
| 5,029,591 A | 7/1991 | Teves | |
| 5,176,698 A * | 1/1993 | Burns | A61M 25/104 |
| | | | 604/913 |
| 5,188,592 A | 2/1993 | Hakki | |
| 5,306,226 A | 4/1994 | Salama | |
| 5,360,402 A | 11/1994 | Conway et al. | |
| 5,441,485 A | 8/1995 | Peters | |
| 5,947,927 A | 9/1999 | Mertens | |
| 6,102,929 A | 8/2000 | Conway et al. | |
| 6,607,546 B1 | 8/2003 | Murken | |
| 6,802,317 B2 | 10/2004 | Göbel | |
| 8,393,328 B2 | 3/2013 | Angel et al. | |
| 2003/0066532 A1* | 4/2003 | Gobel | A61M 16/04 |
| | | | 128/207.15 |
| 2004/0243172 A1 | 12/2004 | Hogle | |
| 2005/0245906 A1 | 11/2005 | Makower et al. | |
| 2007/0277830 A1 | 12/2007 | Ladru et al. | |
| 2008/0125757 A1 | 5/2008 | Gobel | |
| 2009/0030370 A1 | 1/2009 | Nishtala et al. | |
| 2010/0022976 A1 | 1/2010 | Weig | |
| 2010/0113939 A1 | 5/2010 | Mashimo et al. | |
| 2011/0218389 A1 | 9/2011 | Göbel | |
| 2012/0145159 A1 | 6/2012 | Yamada | |
| 2013/0146062 A1 | 6/2013 | Schumacher et al. | |
| 2015/0065810 A1 | 3/2015 | Edgren et al. | |
| 2017/0333654 A1* | 11/2017 | Gobel | A61M 16/044 |

FOREIGN PATENT DOCUMENTS

| | | |
|---|---|---|
| DE | 4010975 A1 | 10/1991 |
| DE | 20320631 U1 | 12/2004 |
| DE | 102011110778 | 1/2013 |
| EP | 0929339 | 2/2003 |
| EP | 1061984 | 6/2004 |
| EP | 1442765 | 8/2004 |
| GB | 2258811 A | 2/1993 |
| WO | WO 2005/120618 | 12/2005 |
| WO | WO 2007/005734 | 1/2007 |
| WO | WO 2008/038172 | 4/2008 |
| WO | WO 2011/139498 | 11/2011 |
| WO | WO 2013/139986 | 9/2013 |
| WO | WO 2016/087926 | 6/2016 |
| WO | WO 2016/087930 | 6/2016 |
| WO | WO 2016/178080 | 11/2016 |

OTHER PUBLICATIONS

Bassi, An In Vitro Study to Assess Determinant Features Associated With Fluid Sealing in the Design of Endotracheal Tube Cuffs and Exerted Tracheal Pressures, Critical Care Medicine, vol. 41, No. 2, 2013, pp. 518-526.

* cited by examiner

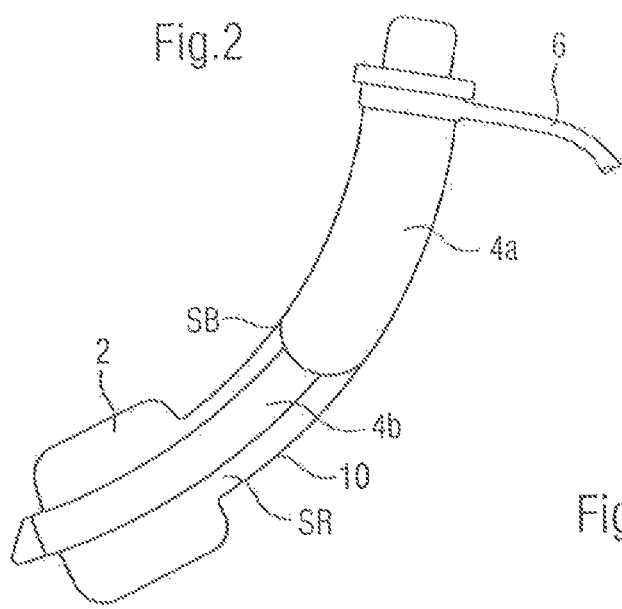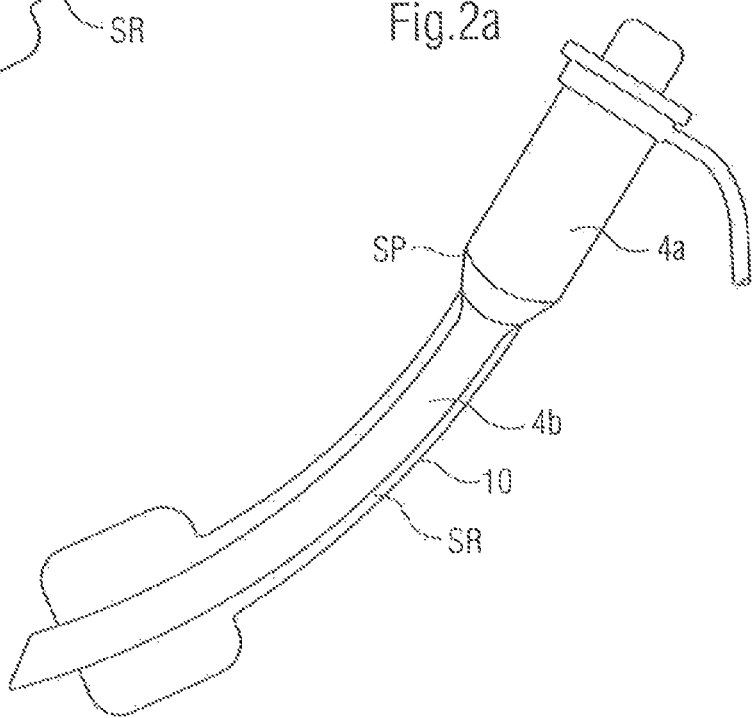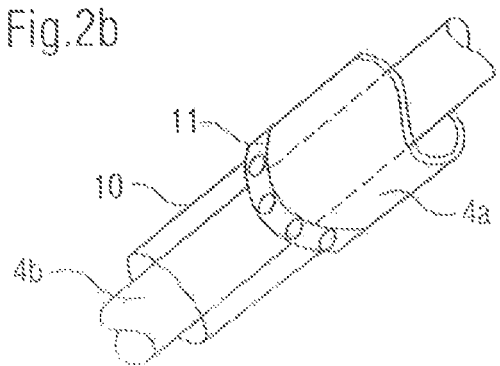

DEVICE FOR A DYNAMICALLY SEALING OCCLUSION OR A SPACE-FILLING TAMPONADE OF A HOLLOW ORGAN

REFERENCE TO PENDING PRIOR PATENT APPLICATIONS

This patent application claims benefit of International (PCT) Patent Application No. PCT/162016/001643, filed 18 Nov. 2016 by Creative Balloons GmbH for DEVICE FOR A DYNAMICALLY SEALING OCCLUSION OR A SPACE-FILLING TAMPONADE OF A HOLLOW ORGAN, which claims benefit of: (i) German Patent Application No. DE 10 2015 014 824.9, filed 18 Nov. 2015 and (ii) International (PCT) Patent Application No PCT/162015/002309, filed 4 Dec. 2015, which patent applications are hereby incorporated herein by reference.

FIELD OF THE INVENTION

The invention is directed primarily to a device for the sealing occlusion and/or space-filling tamponade of a hollow organ or some other cavity in the human body, preferably for the tamponade of an autonomously motile or correspondingly motile or mobile organ and/or for the dynamically sealing intubation of a hollow organ, in particular for the tracheal intubation and ventilation of a patient for rapid volume-compensating sealing of the trachea, using a preferably fully and residually formed balloon that abuts the wall of the organ to be occluded or tamponaded with a sealing pressure of the balloon that is as constant as possible.

BACKGROUND OF THE INVENTION

A fundamental problem with the sealing occlusion or space-filling tamponade of hollow organs or other cavities in the human body results from the specific physiological dynamics of the organ or space in question. Organs that are limited by musculo-connective tissue generally have autonomous motility to a great extent, but may also be subjected to corresponding effects from adjacent motile structures. For an efficient seal and/or tamponade, these types of autonomously motile or correspondingly motile organs or spaces require a particular regulating mechanism that follows the particular dynamics and compensates for functional fluctuations, and which offsets, as synchronously as possible, changes in the diameter or shape of the organ, the tone of the organ, or the particular prevailing internal pressure of the organ, preferably continuously and with the least possible outlay of equipment.

The challenge of dynamic, synchronized adaptation of a balloon seal or tamponade may be illustrated with the example of the human trachea. The trachea is a tube-like structure with portions composed of cartilaginous tissue, connective tissue, and muscle. It extends from the lower section of the larynx to the branching of the main bronchi. The front and side portions of the trachea are stabilized by clip-like, approximately horseshoe-shaped cartilaginous structures, which in turn are connected to one another by layers of connective tissue. The tracheal lumen is closed off on the dorsal, open side of the cartilage rings by the so-called pars membranacea, which consists of material made of continuous musculo-connective tissue, without reinforcing elements. The esophagus, which is made of musculo-connective tissue, and which likewise contains no cartilaginous elements, lies on the dorsal side of the pars membranacea.

The upper third of the trachea is generally located outside of the thorax, while the lower two-thirds lies within the thoracic cavity delimited by the thorax and the diaphragm. The thoracic portion of the trachea is thus in particular subjected to the dynamic pressure fluctuations in the thoracic cavity that occur in the thorax as part of the physiological respiratory activity of a spontaneously breathing patient, or also of a patient who is spontaneously breathing with assistance. The same applies for the esophagus, which extends along the entire length of the thorax. Measurements of the so-called intrathoracic pressure, an important parameter for ventilation design, generally take place using pressure-sensitive measuring devices that are placed in the esophagus, since the thoracic pressure fluctuations caused by respiratory mechanics may be detected with the best possible approximation here due to the soft tissue character of the organ.

During breathing (inspiration), the thoracic volume is enlarged by the lifting of the ribs and the simultaneous lowering of the diaphragm, resulting in a drop in the intrathoracic pressure in the thorax. This drop in pressure produced in the thorax due to respiratory mechanics results in a slight widening of the tracheal lumen in the thoracic portions of the trachea. During tracheal intubation with conventional ventilation catheters, the trachea-sealing cuff is typically placed in the region of the transition of the middle third to the lower third of the trachea. Cuffs positioned in this way may be exposed to the described cyclical widenings of the trachea that are synchronous with the breathing, resulting in corresponding cyclical fluctuations in the cuff sealing pressure. The main task of cuff balloons on the one hand is to protect the deep airways against inflowing secretions from the throat, and on the other hand, to seal the lower airways with positive ventilation pressure during ventilation. The fluctuations in the thoracic pressure caused by the patient's own breathing may move the sealing pressure in the cuff into critically low ranges, in which a sufficient seal against secretions from the throat or the digestive tract is no longer ensured, and the patient aspirates the stomach contents, for example.

Whereas the achievable sealing performance of conventional PVC cuff balloons correlates very closely with the instantaneous filling pressure in the balloon, in particular thin-walled balloon components made of polyurethane (PUR) demonstrate significantly better and more stable sealing efficiency in the course of the pressure cycle.

Secretion sealing of tracheal ventilation catheters is particularly critical in the cuff filling pressure range of 5 to 15 mbar. Although seal-optimized catheter types with microthin-walled PUR cuffs still ensure good sealing performance here, the achievable results are not adequate for aspiration protection for the prevention of infection.

The prior art describes various technical embodiments of filling pressure-regulating devices for tracheal ventilation catheters which provide synchronous, dynamic adjustment of the sealing pressure in the tracheal cuff. The various technologies are based on combined use with tracheal ventilation catheters having a conventional design. In these designs, the trachea-sealing cuffs are filled using a very small-bore filling line that is extruded into the shaft of the catheter or integrated in some other way. This filling line generally does not allow a sufficiently large volume flow of the medium, that acts with pressure on the balloon, in order for the trachea-sealing filling pressure to be adjusted with a sufficiently low latency. Thus, virtually independently of the type and operating principle of the mechanism, a device placed outside the body for prompt volume compensation in the trachea-sealing cuff can achieve a delayed volume compensation that is only partially effective in sealing. Even technically complicated systems designed for rapid regulation, such as the CDR 2000 device from Logomed GmbH, are inadequate with regard to the achievable sealing performance due to the resulting sluggishness in combination with conventional ventilation catheters.

The problem on which the invention is based results from the fact that a sealing technology that is sealing-efficient, synchronously follows the motility of a hollow organ of a patient to be occluded or tamponaded, and compensates for pressure fluctuations has thus far not been found in the prior art.

For a generic device, this problem is solved by an isobarically acting regulator for the filling pressure within the interior of the balloon, comprising a volume reservoir situated extracorporeally outside of the body, and a feed line for communicatively connecting the extracorporeal volume reservoir of the regulator to the interior of the balloon, the connecting feed line between the balloon and the regulator having a flow-directing one-way valve that prevents backflow from the balloon to the volume reservoir of the regulator, while a nonflow-directing throttle element is situated in parallel which allows slow volume compensation between the balloon and the volume reservoir.

As a result of this structure, if the volume within the hollow organ increases, the filling pressure within the sealing balloon may be rapidly increased, since the flow-directing one-way valve then opens due to the pressure drop in the balloon; otherwise, in particular for a reduction of the volume within the hollow organ, the filling pressure within the balloon decreases only gradually.

SUMMARY OF THE INVENTION

The present invention describes a novel catheter technology having a special design of the feed line of the filling medium for the trachea-sealing cuff balloon, which for the first time allows an efficient, sufficiently rapid volume flow between a regulation mechanism external to the body and the cuff placed in the trachea. Based on such a flow-optimized feed line or communication between the regulator and cuff, technically simple devices for regulating volume or cuff pressure may be used which achieve sealing of the cuff synchronously with the breathing, without complicated electronic or mechanical control systems, and which thus also allow single-use approaches that are fixedly connected to the particular catheter.

The invention describes these types of single-use components for isobaric volume compensation, but alternatively is also directed to possible electronic approaches to cuff pressure stabilization in conjunction with the flow optimization, according to the invention, of the sealing medium.

In addition to the optimized communication of the sealing medium between the extracorporeally regulating unit and the trachea-sealing unit, the invention also describes derived designs of ventilation catheters for ensuring the largest possible inner lumens for preferably low-resistance tracheal ventilation or spontaneous breathing of patients.

Furthermore, the invention describes designs that avoid the pooling of secretions in the space between the cuff and vocal folds in order to avoid other potentially traumatizing relative movements between the catheter shaft and the structures of the larynx.

In addition to flow-optimized, catheter shaft-integrated feed lines between the regulator and the cuff, the invention describes special tracheal balloon components that are tightly sealingly attached to the distal end of the ventilation catheter and to the shaft body, and which in the area of the transition from the thoracic to the extra-thoracic section of the trachea, in the area of the vocal folds, or also in the area of the lower throat, narrow approximately to the outer dimensions of the catheter shaft but leave a gap, preferably free on all sides, between the sleeve of the proximal portion of the balloon element thus narrowed, and the shaft that is enclosed by the sleeve. This gap-like space provided around the catheter shaft allows a particularly large-bore, rapid volume flow of the sealing medium.

At the proximal end of the balloon that is narrowed in this way, the gap space transitions into a shaft structure that is correspondingly equipped for preferably delay-free, flow-optimized supplying of filling medium, or has appropriately flow-optimized supply channels that are integrated into the shaft body.

The transition of the proximal end of the balloon to the accommodating shaft structure preferably takes place beneath the vocal folds (subglottal), or optionally also above the vocal folds (supraglottal).

The concentric arrangement of the catheter shaft within a tapered hose-like balloon segment is advantageous in particular in the area of the vocal folds. The hose-like balloon sleeve protectively lies against the sensitive structures of the inner larynx, and avoids a direct, mechanically traumatizing effect of the catheter shaft.

As a further design variant of a trachea-sealing balloon component, the invention proposes a cuff-in-cuff arrangement as already presented in EP 1061984 B1. This particular design of two internested cuffs, in addition to the tracheal sealing by an inner balloon that is stabilized according to the invention at a relatively higher sealing pressure, also allows tamponading of the subglottal space by an outer balloon at a relatively lower tamponade pressure. As a result of the extra-thoracic positioning of the outer subglottally or also glottally tamponading sleeve in the upper third of the trachea, there is only moderate transfer of thoracic pressure fluctuations to the prevailing tamponade pressure, so that the tamponade pressure may be held in a very low filling pressure range with protection of tissue, without relevant pressure loss. In addition to the nested arrangement, a sequential arrangement of the trachea-sealing cuff (distal) and the subglottal tamponade balloon (proximal), without a space in between, is conceivable.

The invention also describes a reservoir unit that is specially designed for this concentric or sequential arrangement, having a double balloon arrangement for separate setting of two different filling pressures.

The volume flow according to the invention between the trachea-sealing balloon body and the extracorporeal regulator may also be achieved, essentially just as efficiently, with tracheal tubes and tracheostomy cannulas having a conventional design, with a cuff balloon on the end, wherein the supply channel to the cuff is integrated into the shaft wall of the catheter shaft, and the supply channel has a cross-sectional area corresponding to a circular cross-sectional area with a circular diameter of at least 2 mm. Sufficient flow is [achieved] with cross-sectional areas having a circular diameter of 3 to 4 mm. For the effect according to the invention, it is presumed that the supplying hose line has an appropriately designed diameter.

The principle according to the invention of stabilizing a sealing pressure by flow-optimized supplying of a filling medium may likewise be advantageously used for the sealing cuffs of supraglottal airways, so-called larynx masks. With sealing bodies having a conventional design, which fix and seal the mask over the larynx, a marked improvement in the sealing efficiency and the dynamics of adjustment to the changing tonicities in the area of the hypopharynx may be achieved here as well by coupling the sealing cuff element to a regulating reservoir unit and incorporating an integrated valve-throttle combination.

In addition to applications in the area of the seal of the upper and lower airways, the principle according to the invention may also be used in transesophageal probes that are equipped with an esophagus-sealing balloon element. The efficiency of the seal here is likewise dependent to a great extent on the capability for the quickest possible volume shift between the extracorporeal reservoir and the sealing balloon.

BRIEF DESCRIPTION OF THE DRAWINGS

Further features, particulars, advantages, and effects based on the invention result from the subclaims and from the following description of preferred exemplary embodiments of the invention, and with reference to the drawings, which show the following:

FIG. 2 shows a tracheal tube with a gap-forming, extended proximal balloon end, which in the subglottal area transitions into the shaft body;

FIG. 2a shows a design corresponding to FIG. 2, but with the extended proximal balloon end in the supraglottal area connected to the shaft body;

FIG. 2b shows an atraumatic transition between the shaft body and the proximal balloon end;

DETAILED DESCRIPTION OF THE PREFERRED EMBODIMENTS

Figure 1:
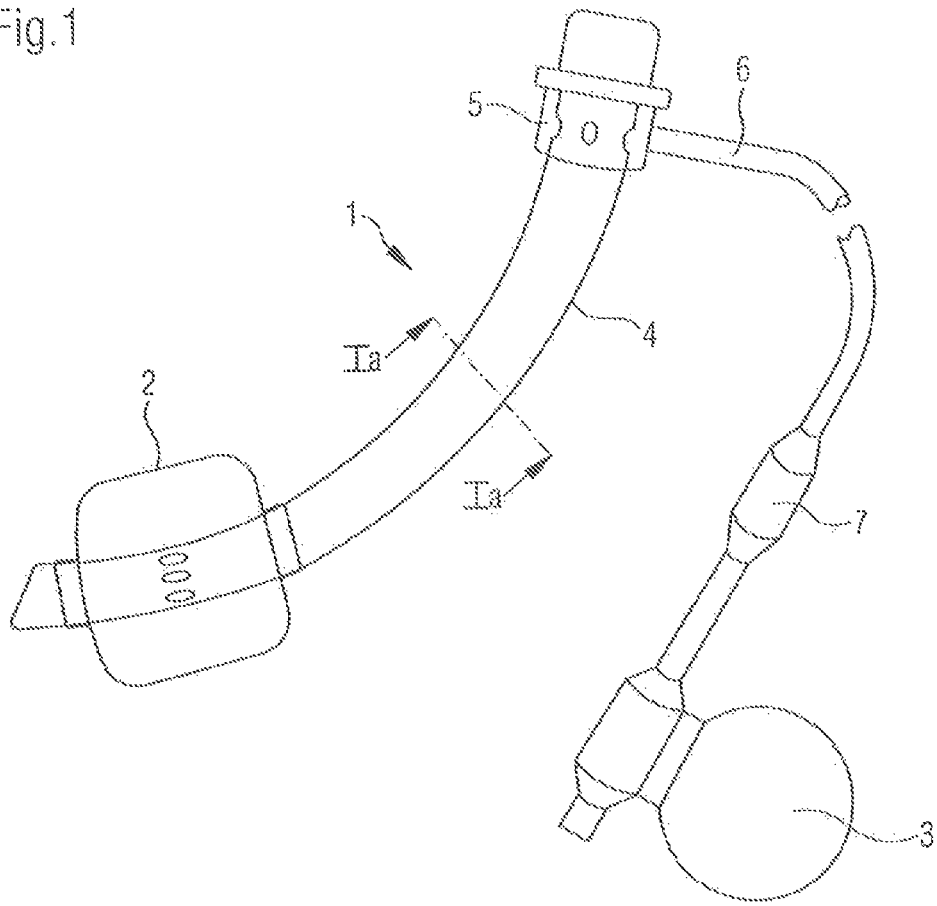
FIG. 1 shows a tracheal tube according to the invention with a continuous feed line integrated into the shaft in combination with an external volume- or pressure-regulating device and a flow-directing device.

FIG. 1 describes, in an illustrative total overview, various function-optimizing components of a tracheal ventilation catheter 1 (tracheal tube) for dynamic tracheal sealing, with cyclically alternating thoracic pressures, by flow-optimized shifting of a filling medium that is acted on by pressure, between a tracheal positioned sealing balloon 2 (cuff) and an extracorporeal regulator or reservoir element 3.

The shape and dimensions of the device according to the invention largely correspond to a conventional tracheal tube. At the distal end of the tube, the trachea-sealing balloon at both its ends is connected with a tight seal to the catheter shaft bearing the balloon. The shaft body 4 preferably has a large-bore or multi-lumen feed line, integrated into the shaft, for the cuff. The respective supply lumens are combined at the proximal shaft end 5, and from there are attached via a large-bore feed line 6 to the regulator element 3. To avoid rapid retrograde emptying toward the reservoir, and also for delayed pressure or volume compensation between the compartments on the end, a combined valve-throttle function 7 is integrated into the feed line. The combination of the communicating volumes of the balloon, feed line, valve-throttle, and reservoir or regulator element results in a shared interior in which a constant pressure, defined by the reservoir or the regulator, is maintained. Within the scope of the invention, air is used as a preferred medium for filling the communicating interior.

The technology described within the scope of the invention, for optimal quick volume shifting with the lowest possible resistance, and at the same time, the lowest possible pressure gradients between a tracheal positioned balloon and an extracorporeal regulator unit, is intended to allow pressure-stabilizing volume compensation within the trachea-sealing balloon, which in the optimal case is terminated after no more than 10 to 20 milliseconds after the onset of a pressure drop that is triggered by respiration mechanics.

Figure 1A:
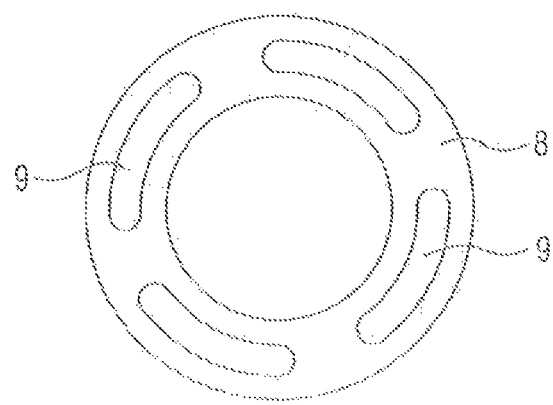
FIG. 1a shows an example of a shaft profile in cross section, corresponding to FIG. 1.

FIG. 1a shows an example of a multi-lumen shaft profile 8 in cross section. The feed line lumens 9 integrated into the shaft wall, in the sense of the smallest possible enlargement of the shaft outer diameter, are preferably flat or designed with the smallest possible radial height. In the base design shown in FIGS. 1 and 1a, PVC is a preferred shaft material for the Shore durometer range of 80 A to 90 A.

FIG. 2 shows a tracheal tube according to the invention, having a trachea-sealing balloon 2 at the distal tube end; the tapered proximal end 10 of the balloon is extended further into the subglottal area SB, where it is accommodated by the proximal shaft portion 4a or is connected to same with a tight seal. The distal shaft portion 4b has a single-lumen design, whereas the proximal portion preferably has a multi-lumen profile corresponding to FIG. 1a. The same as in FIG. 1, the filling medium is thus supplied to the proximal balloon end in a flow-optimized manner. The hose-like tapered balloon end 10 creates a large-bore gap space SR between the hose sleeve and the shaft which freely communicates with the sealing body, thus allowing very advantageous flow resistances that are low according to the invention.

FIG. 2a shows a tracheal tube corresponding to FIG. 2, in which the transition or the connection of the proximally extended end of the balloon 10 which forms a gap space relative to the shaft takes place in the supraglottal area SP, i.e., above the vocal folds. The flow-effective cross section of the gap space SR that results with this design should at least correspond to the flow-effective cross section of the sum of the supply lumens integrated into the shaft, and in turn should at least correspond to the flow-effective cross section of the hose connection between the tube shaft and the regulator unit.

The hose-like balloon end 10 that is extended in the proximal direction may be created directly from the trachea-sealing balloon body when it is formed, or, as a separately manufactured hose-like element, may be attached to the proximal end of the sealing body, for example by gluing. The balloon end is likewise preferably made of polyurethane having a small wall thickness of 10 to 50 μm, particularly preferably 10 to 30 μm.

FIG. 2b shows the subglottal or supraglottal transition from the proximal balloon end 10 to the proximal shaft end 4a in a design by way of example. The transition 11 of the proximal shaft end 4a to the distal shaft end 4b preferably has an atraumatic conical design. The lumens 9 integrated into the shaft open into the gap space SR via the conical taper.

Figure 2C:
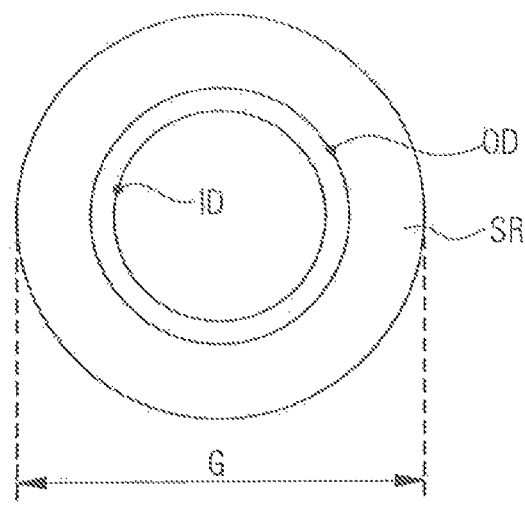
FIG. 2c shows advantageous proportions of the gap space relative to the diameters of the tube shaft.

For the dimensioning of the gap space in the area of the proximal balloon extension 10, FIG. 2c shows the preferred dimensional ratios of the volume-shifting cross-sectional area of the gap space SR to the cross-sectional area of the ventilation lumen ID, and to the total cross-sectional area OD of the catheter. The gap surface S illustrated in FIGS. 2 and 2a results from the difference between the diameter of the cross-sectional area G specified by the sleeve wall in the area 10 and the cross-sectional area OD of the shaft body delimited by the outer surface of the shaft. The gap surface S should be 1/10 to 5/10 of the cross-sectional area G, particularly preferably 2/10 to 3/10 of the cross-sectional area G. Relative to the cross-sectional area ID of the inner lumen of the shaft body, the gap surface S should be 2/10 to 6/10 of the cross-sectional area ID, particularly preferably 3/10 to 4/10 of the cross-sectional area ID.

Figure 2D:
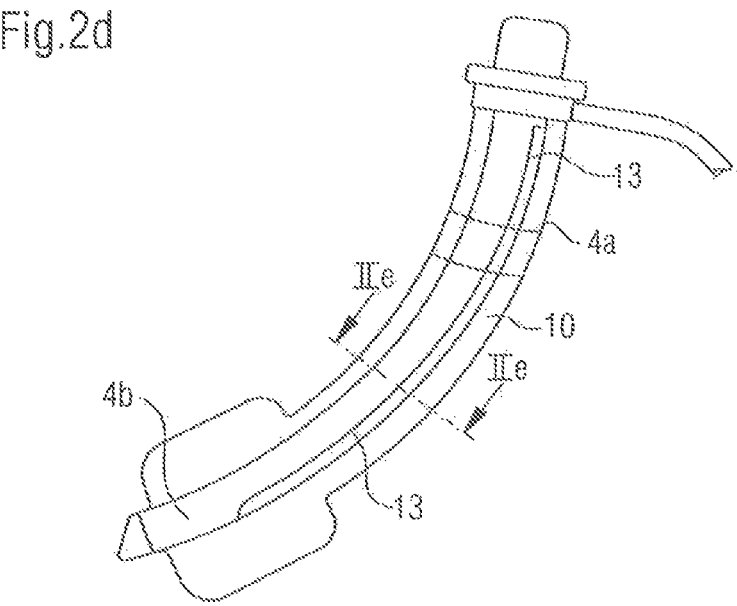
FIG. 2d shows a grooved pre-formation of the shaft body for shifting the volume.

FIG. 2d shows a particular design detail of the shaft body 4, which ensures an unhindered volume flow across the anatomically narrow vocal fold plane, in particular for the design of the device according to FIG. 2a. The illustrated recess 13 may be made up, for example, of one or more grooved indentations extending in the shaft longitudinal axis. The recess is intended to ensure that a sufficiently rapid volume flow is able to communicate between the regulator and the sealing balloon, even in the event of a transient or permanent closure of the volume-shifting gap space. For example, a tubing network 14 or a corresponding hose element having a sieve-like perforation may be inserted into the recess, which keeps the recess open. The recess may contribute to stabilization of the tube shaft against buckling and twisting in a preferred positioning at the apex of the large curvature.

Figure 2E:
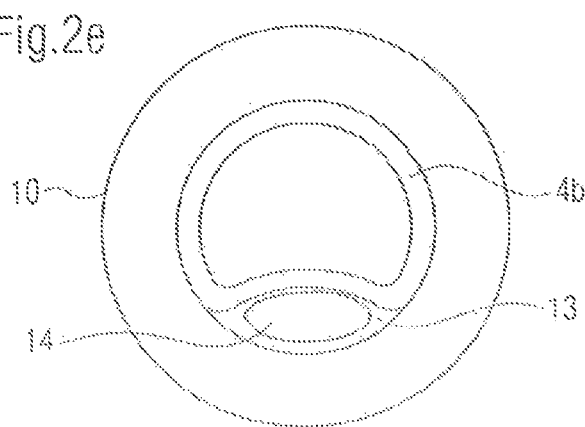
FIG. 2e shows a cross section of the pre-formation shown in FIG. 2d.

FIG. 2e shows the recess in the shaft body 4 in cross section.

The following place-holder values should be used for an exemplary quantitative calculation of the flow conditions in a cylindrical shell-shaped gap space SR defined in FIGS. 2 and 2a, in particular [based] on the pressure ratios in the distal trachea-sealing balloon section 2:

$V_1$ volume of the trachea-sealing balloon 2
$P_1$ pressure in the trachea-sealing balloon 2
$\rho_1$ filling density in the trachea-sealing balloon 2
$M_1$ air mass in the trachea-sealing balloon 2
$V_2$ volume of the extracorporeal reservoir 3
$P_2$ pressure in the extracorporeal reservoir 3
$\rho_2$ filling density in the extracorporeal reservoir 3
$m_2$ air mass in the extracorporeal reservoir 3

The following applies for the air masses $m_1$, $m_2$:

$$m_1(t) = m_{1,0} \int_{T=0}^{T=t} S_{m,1}(T) dT \tag{1}$$

$$m_2(t) = m_{2,0} - \int_{T=0}^{T=t} S_{m,2}(T) dT \tag{2}$$

$S_{m,v}$ stands for the air flow to the respective balloon 2, 3 as an air mass flow.

According to the Hagen-Poiseuille law, the following is true for the mass fluid flow through a line having an inner radius R and a length l:

$$S_{m,1} = \frac{\rho_1 \cdot \pi (p_2 - p_1) \cdot R^4}{8\eta \cdot l} \tag{3}$$

$$S_{m,2} = \frac{\rho_2 \cdot \pi (p_1 - p_2) \cdot R^4}{8\eta \cdot l} \tag{4}$$

$\eta$ stands for the dynamic viscosity of the flowing gas. For air:
$\eta$ is 17.1 μPa·s at 273 K Furthermore, based on the thermal equation of state of ideal gases, the following applies in the balloon 2:

$$\eta_1 = \rho_1 \cdot R_S \cdot T_1 \tag{5}$$

and in the reservoir 3:

$$\eta_2 = \rho_2 \cdot R_S \cdot T_2 \tag{6}$$

$R_S$ is the individual or specific gas constant, which for air has the value 287.058 J/(kg·K).
$T_v$ is the temperature in the balloon 2 and in the reservoir 3.

For a temperature of 23° C. or 296 K, the factor is $$k = R_{S,air} \cdot T_{23° C.} = 85 \cdot 10^3 \text{ J(kg·K)} \tag{7}$$

It should be assumed below that the temperature in the balloon 2 and also in the reservoir 3 is constant at 23° C.

$$T_1 = T_2 = 296 \text{ K}$$

The following then applies:

$$\rho_1 = p_1 \cdot k \tag{8}$$

$$\rho_2 = p_2 \cdot k \tag{9}$$

Thus, by inserting equation (3) into equation (1), the result is:

$$m_1(t) = m_{1,0} + \int_{\tau=0}^{\tau=t} \frac{\rho_1 \cdot \pi \cdot R^4}{8\eta \cdot l} (p_2 - p_1) d\tau \tag{10}$$

With equation (8), it follows that:

$$m_1(t) = m_{1,0} + \int_{\tau=0}^{\tau=t} \frac{\rho_1 \cdot \pi \cdot R^4}{8\eta \cdot l \cdot k} p_1 (p_2 - p_1) d\tau \tag{11}$$

In addition, in the balloon (2) the following applies:

$$\frac{m_1}{V_1} = \rho_1 = \frac{p_1}{k} \quad (12)$$

Therefore, the following can be written in equation (11) for the mass $m_1$:

$$m_1 = \frac{V_1 \cdot p_1}{k} \quad (13)$$

The result is:

$$\frac{V_1}{k} \cdot p_1(t) = \frac{V_1}{k} \cdot p_{1,0} - \int_{\tau=0}^{\tau=t} \frac{\pi \cdot R^4}{8\eta \cdot l \cdot k} \cdot [p_1^2 - p_1 p_2] d\tau \quad (14)$$

The entire equation can be shortened to $V_1/k$. Differentiation on both sides results in:

$$\frac{dp_1}{dt} = -\frac{\pi \cdot R^4}{V_1 8\eta l} \cdot [p_1^2 - p_1 p_2] \quad (15)$$

This is a Bernoulli differential equation of the form:

$$x' = -a \cdot x \cdot (x - b), \text{ where} \quad (16)$$

$$a = \frac{\pi \cdot R^4}{V_1 8\eta l} \quad (17)$$

$$b = p_2 \quad (18)$$

It should be assumed below that the reservoir 3 is significantly larger than the balloon 2:

$$V_2 \gg V_1$$

From this it follows that the pressure $\rho_2$ in the reservoir 3 remains essentially constant, even when the pressure $p_1$ in the balloon 2 briefly changes. Under this assumption, the coefficients a and b from the Bernoulli differential equation (16) are constant, and the solution to the Bernoulli differential equation is:

$$x(t) = \frac{b}{1 - e^{-abt - bc_1}} \quad (19)$$

The integration constant $c_1$ may be determined as follows:

$$p_1(t) = \frac{p_2}{1 - e^{-ap_2 t - p_2 c_1}} \quad (20)$$

For t=0, the following must apply:

$$p_1(t) = p_{1,0} \quad (21)$$

The result is:

$$p_{1,0} = \frac{p_2}{1 - e^{-p_2 c_1}} \quad (22)$$

$$\frac{p_2}{p_{1,0}} = 1 - e^{-p_2 c_1} \quad (23)$$

$$e^{-p_2 c_1} = \frac{p_{1,0} - p_2}{p_{1,0}} \quad (24)$$

$$-p_2 c_1 = \ln \frac{p_{1,0} - p_2}{p_{1,0}} \quad (25)$$

$$c_1 = -\frac{1}{p_2} \cdot \ln \frac{p_{1,0} - p_2}{p_{1,0}} = \frac{1}{p_2} \cdot \ln \frac{p_{1,0}}{p_{1,0} - p_2} \quad (26)$$

Inserted into equation (2), this provides:

$$\frac{p_1(t)}{p_{1,0}} = \frac{p_2}{p_{1,0} - [p_{1,0} - p_2] \cdot e^{-(\pi R^4 p_2 t)/(8 V_1 \eta l)}} \quad (27)$$

This equation is of the form:

$$\frac{p_1(t)}{p_{1,0}} = \frac{p_2}{p_{1,0} - [p_{1,0} - p_2] \cdot e^{-t/\tau}} \text{ where} \quad (28)$$

$$\tau = (8 V_1 \eta l)/(\pi R^4 p_2) \quad (29)$$

The following, for example, applies for minor pressure fluctuations in the balloon 2:

$$P_{1,0} \approx 0.99 \rho_2$$

Moreover, for t=τ:

$$e^{-t/\tau} = e^{-1} \approx 0.37$$

And for t=4τ:

$$e^{-t/\tau} = e^{-4} \approx 0.018$$

In equation (28) this yields:

$$\frac{p_1(t = 4\tau)}{0.99 p_2} = \frac{p_2}{0.99 p_2 - (0.99 p_2 - p_2) \cdot 0.018} \text{ or:}$$

$$p_1(t = 4\tau) = p_2 \cdot \frac{0.99}{0.99 + 0.018 + 0.01} = 0.9998 \cdot p_2,$$

respectively.

This is only 2% of the initial deviation.

When applied within the framework of respiration, it should be noted that a breathing cycle lasts about 3 sec. So that the cuff does not develop leaks during this period, this compensation time should be t=4 τ≈8 ms.

This results in:

$$\tau = 2 \cdot 10^{-3} \text{ s} = \frac{8 \cdot 5 \cdot 10^{-6} \text{ m}^3 \cdot 0.2 \text{ m} \cdot 17.1 \cdot 10^{-6} \text{ Pas}}{\pi \cdot R^4 \cdot 10^5 \text{ Pa}}$$

for which it was assumed:

$V_1 = 5$ cm$^3$ $l = 20$ cm $p_2 = 10^5$ Pa

This results in:

$R^4 = 0.7 \cdot 10^{-12}$ m$^4$, that is, $R = 0.91 \cdot 10^{-3}$ m $\approx 1$ mm.

Since the flow conditions in a cylindrical shell-shaped cavity are much poorer than in a cylindrical cavity, the radial cross section of cylindrical shell-shaped cavity should be significantly larger. In addition, the feed lines 6 and 9 were likewise disregarded in the above calculation, which, however, represents a flow resistance that is not insignificant. Therefore, the radial height of the cylindrical shell-shaped gap space 10 should be at least 2 mm, or even better, 3 to 4 mm.

Figure 3:
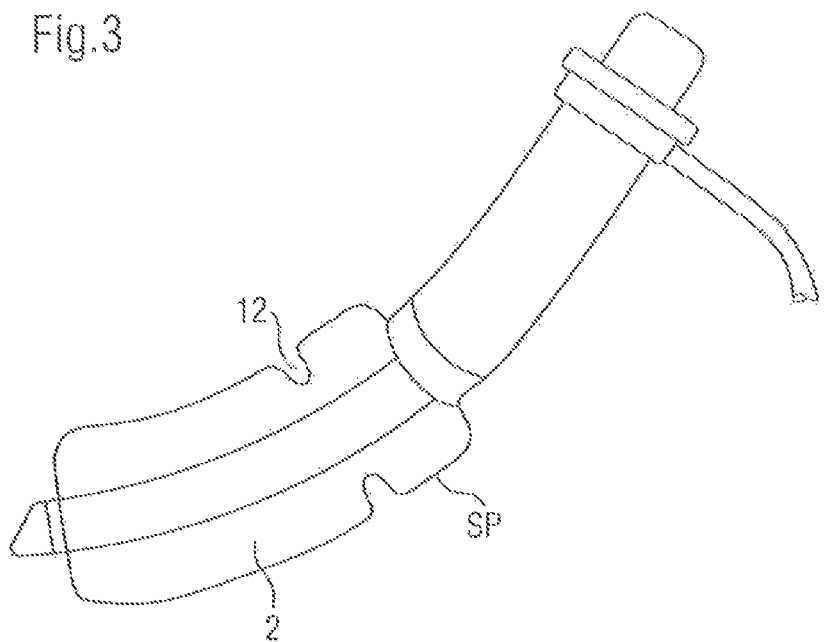
FIG. 3 shows a single-chamber balloon that is tracheal sealed as well as subglottally tamponaded.

FIG. 3 shows a tracheal tube having a balloon element 2 that is extended beyond the plane of the vocal folds. The balloon element, corresponding to the other embodiments described within the scope of the invention, should preferably be made of molded film material, whose diameter has a residual dimension such that the balloon element does not have to be stretched in order to seal the tracheal lumen, and the mucosa of the organ make close contact, largely without tension, when the excess portion of the balloon sleeve is folded in. Polyurethane-based balloon films having a wall thickness of preferably 5 to 20 μm, less preferably 20 to 50 μm, in the area of the trachea-sealing balloon segment are preferred in the invention.

Polyurethanes having Shore hardnesses of 70 A to 95 A or 55 D to 65 D are preferably used according to the invention for the trachea-sealing balloon element. Shore hardnesses in the range of 85 A to 95 A are particularly preferably used.

Although in the simple case the balloon element is dimensioned for sealing in the area of the transition from the lower third to the middle third of the trachea, as is common in conventional tracheal tubes or tracheal cannulas, within the scope of the invention the trachea-sealing balloon segment may also be extended in the proximal direction, reaching beyond the vocal folds into the area of the supraglottal lower throat. The body of the balloon element 2 preferably has a cylindrical shape, and in the area of the vocal fold plane may be provided with a circular taper 12 for accommodating the vocal folds.

The design of the trachea-sealing balloon extended in the proximal direction allows a particularly large balloon volume that is capable of developing a certain pressure-maintaining buffer effect when enlargements of the tracheal cross section caused by respiratory mechanics, or a reduction in transmural force acting on the trachea-sealing balloon, occurs in the tracheal section of the balloon body. If the proximal balloon end extends out of the thorax, this extrathoracic segment of the thoracic respiratory mechanics is not exposed, which correspondingly assists with the damping effect of the extracorporeal volume reserve, and the dynamically acting, seal-maintaining function of the device according to the invention is further improved.

In addition, due to the large contact surface of a trachea-sealing balloon extended in the proximal direction, the largest possible migration path for secretions and pathogens contained therein is made possible.

Figure 3A:
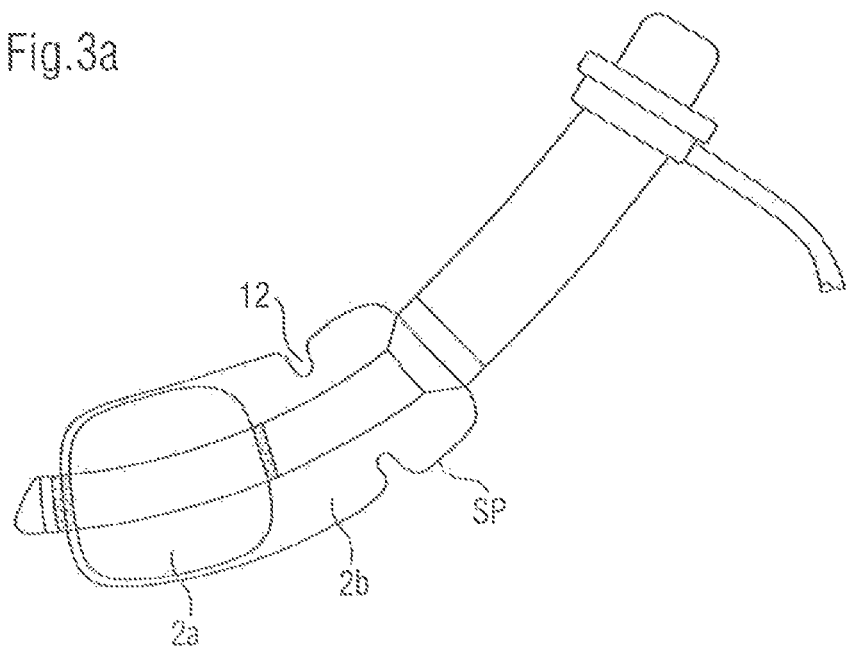
FIG. 3a shows a double-chamber arrangement with a tracheal sealing and a subglottally to supraglottally tamponading balloon.

FIG. 3a shows a tube corresponding to FIG. 3, containing two internested cuffs, and which, in addition to the tracheal sealing by an inner balloon 2a at a relatively higher sealing pressure, also allows tamponading of the subglottal space by an outer balloon 2b at a relatively lower tamponade pressure. In addition to the concentric arrangement, a sequential arrangement of the trachea-sealing cuff (distal) and subglottal tamponade balloon (proximal), without a space in between, is conceivable.

Figure 4:
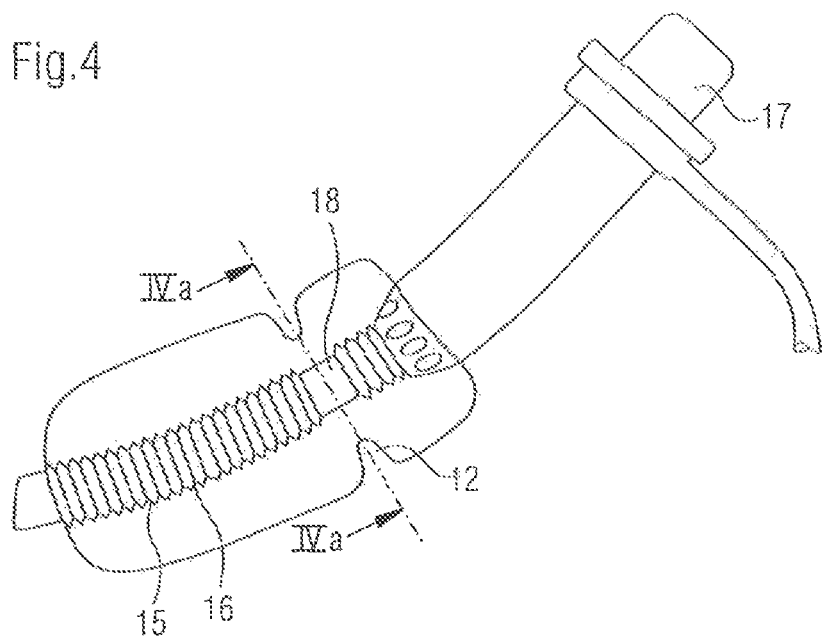
FIG. 4 shows a tracheal tube having a two-part shaft body whose supraglottal section is designed as a particularly stable bite protector, and whose shaft adjoining in the distal direction has a single-lumen segment with a maximized inner diameter.

In the design illustrated in FIG. 4, the catheter shaft 4 used for the tracheal ventilation device is likewise made of polyurethane (PUR), since PUR, with an appropriate combination of material hardness and machining, such as profiling of the surface of the shaft, provides the option for manufacturing very thin-walled shafts which still have good anti-kink stability. In comparison to alternative materials such as silicone or PVC, this allows larger inner lumens that improve the flow resistance of the respiratory gas. Since the shaft has no filling line integrated into the shaft wall for the sealing cuff, as is common in conventional tube shafts, the inner lumen of the shaft that is active in ventilation may be correspondingly enlarged, and thus, the flow resistance during respiration or ventilation of the patient may be optimally reduced to a great extent.

For stabilizing the shaft lumen and for allowing essentially tension-free axial bending of the shaft during placement in the airways, the particularly thin-walled shaft body 15 with a single-lumen design is provided with an undulating corrugation 16 on its surface. In the preferred case, it should be possible to axially bend the shaft from 90 to 180 degrees without relevant lumen constriction, and without elastic restoring forces, which are typical for polyurethane, acting on the tissue, which could potentially be traumatic. The shaft may thus optimally follow movements of the patient or relative movements between the shaft and the patient.

For inner shaft diameters of 7-10 mm, with a combination of a wall thickness of approximately 0.3 to 0.5 mm, a Shore hardness value of 95 A to 75 D, a peak-to-peak corrugation spacing of 0.3 to 0.8 mm, and a corrugation amplitude of 0.5 to 1 mm, it is possible to produce a correspondingly kink-resistant, lumen-optimized shaft.

The corrugation may be limited to the tracheal section of the tube shaft, but may also extend to the subglottal area or across the entire length of the shaft to the proximal end of the shaft and the connector 17 mounted at that location.

In the case of the corrugated design of the shaft 4, when an exchangeable inner cannula is used, such as those common in tracheostomy cannulas, it is possible to use an inner cannula with a congruently corrugated profile, whose corrugation optimally conforms to the corrugation of the outer cannula and advantageously reinforces and stabilizes the outer cannula with a small combined wall thickness of the outer and inner cannulas, and thus allows partial wall thicknesses, for example, of 0.3 to 0.5 mm for the outer cannula and 0.1 to 0.3 mm for the inner cannula.

The illustration shows a combined design of the shaft body, which has tracheal and glottal segments made of a single-layer, inner diameter-optimized shaft material, and which in the supraglottal segment transitions into a solid, for example injection-molded, PVC portion which, as illustrated in FIG. 1a, may be provided with multiple lumens 9 for the feed line to the balloon element. In particular, the subglottal portion may be strengthened by a possible reinforcing or multilayer design, so that it is used as a bite protector and thus, in particular for vigilant patients, avoids lumen closure of the tube when the jaws are closed.

Figure 4A:
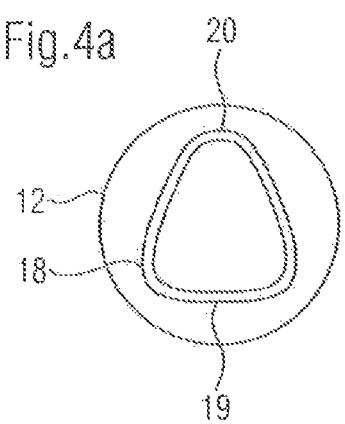
FIG. 4a shows a triangular shaft segment for positioning in the glottis.
Figure 5:
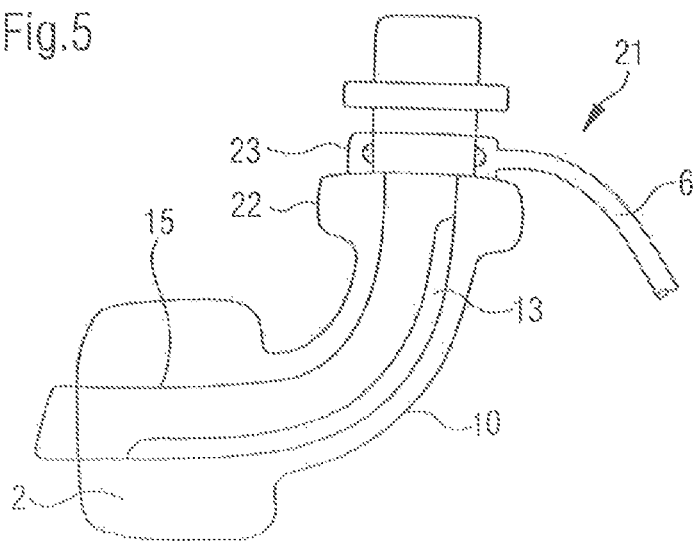
FIG. 5 shows a tracheal cannula having a proximal balloon that is extracorporeally extended.

FIG. 4a shows a cross section of the embodiment in FIG. 5 in its glottal segment 18. The profile of the shaft may have a triangular design here, so that it rests with its base 19 on the dorsal surface of the vocal fold plane, and with its apex 20 points in the ventral direction, thus optimally adapting to the triangular opening of the vocal folds.

FIG. 5 shows an example of an application of the invention for a tracheostomy cannula 21. Similar to the design for tracheal tubes, the proximal balloon end 10 here is guided through the stoma to the trachea. The balloon end may form a ridge-like widening 22 in front of the stoma. The proximal widening may be designed as a ridge-like widening, upon which connector 23 rests, which via a ring-like sealing lip 23 allows free movability of the connector on the shaft. The proximal widening may thus be pushed toward the stoma, and the device may thus be adapted to the particular neck anatomy.

To ensure the sufficiently rapid volume flow of the filling medium between all intracorporeal portions of the cannula resting on the balloon 2, the balloon is preferably provided with a grooved, optionally reinforced recess, as described for FIG. 2c.

In terms of the largest possible inner diameter, and thus, the lowest possible respiration or ventilation resistance, the shaft body 4 of the cannula is likewise preferably made of thin-walled PUR having a corrugated profile, as described for FIG. 4.

Figure 6:
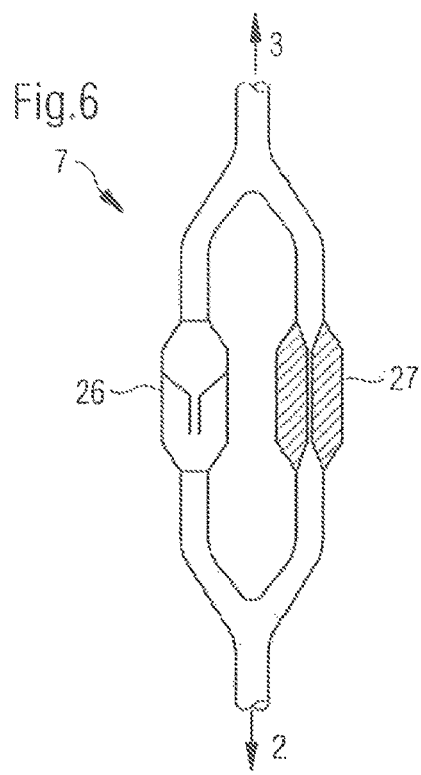
FIG. 6 shows a combined valve/throttle mechanism.

With reference to FIG. 6, to avoid sudden, retrograde, potentially seal-critical emptying of the balloon volume toward the regulator or the reservoir, which may occur, for example, when the patient coughs several times in quick succession, the connecting feed line 6 between the shaft and the regulating reservoir unit may be equipped with a flow-directing valve 26 that prevents the rapid backflow of filling medium. The valve should be designed in such a way that it impairs the open anterograde volume flow from the regulator toward the balloon as little as possible.

To avoid pooling effects of medium in the balloon caused by the valve 26, the valve is preferably equipped with a nonflow-directed bypass throttle 27 that is open on both sides, and which allows a slow, delayed pressure or volume compensation between the two end-side compartments of the balloon 2 and the regulator 3. In the simplest embodiment, the sealing valve surface in question is provided with a small borehole or opening that allows an appropriate throttled volume flow.

Figure 7:
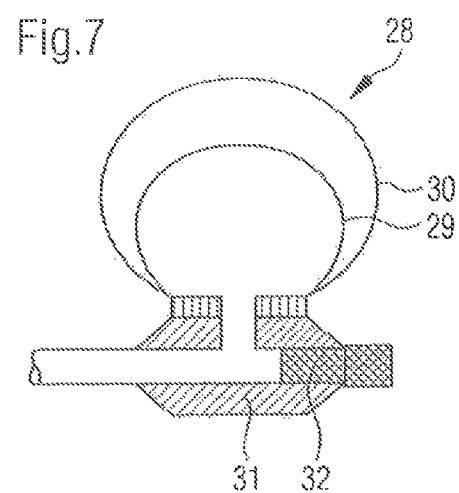
FIG. 7 shows an example of a regulator or reservoir component.
Figure 7A:
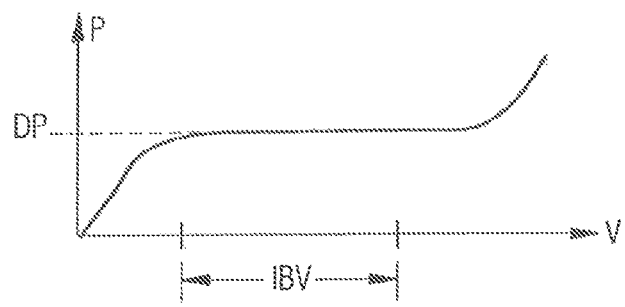
FIG. 7a shows a pressure-volume curve associated with the component described for FIG. 7.

FIG. 7 describes an example of a design of a combined regulator and reservoir unit 3. The unit has some design features of a so-called Lanz regulator (see US . . . ). The essential functional component of the unit 3, the same as for the unit according to Lanz, comprises a special volume-expandable balloon bladder 28 made of highly elastic material, and which due to filling, transitions from a certain preformed, for example spherical, base or resting shape 29 into a stretched working shape 30. When suitable materials are used, a certain expansion behavior of the balloon bladder may be achieved, in which the volume increases with isobaric pressure development in the balloon. The associated conceptually desired pressure-volume curve is illustrated in FIG. 7a. The balloon bladder is preferably made of a natural latex-like material or a synthetic material, such as an isoprene-related material. The balloon bladder rests on a pedestal housing 31 in which a one-way valve 32 for filling with air is preferably installed.

FIG. 7a shows a pressure-volume curve as an example of FIG. 7, and which provides a constant pressure over a specified volume range VP. Thus, a volume of the balloon 2 may flow out of the expanded balloon 30, without a pressure loss resulting due to the volume outflow in the reservoir, i.e., leaving the pressure plateau DP. For applications of this regulator technology with ventilation tubes, the isobaric volume range IBV which is settable in this way should correspond approximately to the freely formed volume of the trachea-sealing balloon.

Figure 7B:
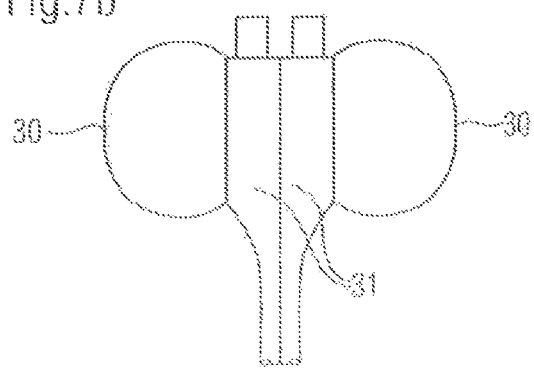
FIG. 7b shows a reservoir balloon or regulator balloon designed for double-chamber systems.

FIG. 7b shows a special double-chamber reservoir balloon arrangement DR, in which two balloon-based reservoirs according to FIGS. 7 and 7a are mounted on a single, shared based housing 33. One chamber allows a trachea-sealing pressure of 25 to 30 mbar, while the other chamber allows the setting of a tamponade pressure of 5 to 15 mbar, for example for the subglottal tamponade as described for FIG. 3a.

Figure 8:
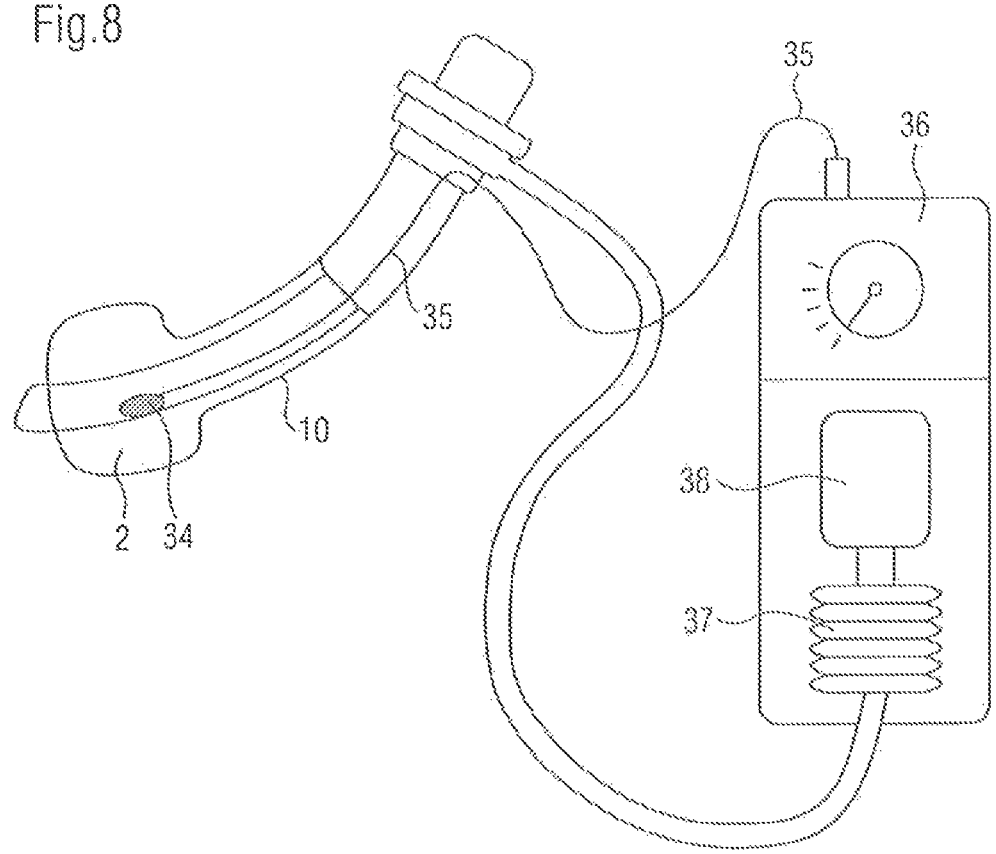
FIG. 8 shows a supply line-optimized tracheal tube according to the invention, with a sensor element in the area of the trachea-sealing balloon segment, and a regulator unit which together with the sensor is situated in a control loop.

FIG. 8 shows a tracheal tube which is provided with a pressure-sensitive or pressure-measuring sensor element 34 inside the trachea-sealing balloon segment 2. In one preferred embodiment, the pressure sensor is an electronic component that relays its measuring signal to an electronically controlled regulator 36 via a cable line 35. The sensor element preferably comprises an absolute pressure sensor. Sensors based on strain gauges or piezoelectric sensors may preferably be used. The regulator 36 has a bellows-like or piston-like reservoir 37, for example, that is actuated by a drive 38 and either shifts volume to the balloon 2 or removes volume from the balloon 2; the drive may, for example, comprise a step motor or may be designed as a linear magnetic drive. The control of the regulator is designed in such a way that deviations in the filling pressure in the area of the sealing balloon segment 2 may be immediately compensated for by a corresponding volume shift, or the filling pressure may be held constant at a setpoint value SW that is settable with the regulator. With this method, the sealing balloon pressure is stabilized at a point in time that is optimally before the mechanical ventilation stroke begins, and before the actual volume flow of respiratory gas into the patient's lungs. This is particularly relevant for patients who must expend increased breathing effort after a long period of controlled machine-assisted ventilation in order to stretch an insufficiently volume-expandable lung to a point that triggers an effective volume flow into the lung. In this phase of the isometric tensioning of the lung within the thorax and the decrease in pressure within the thorax that accompanies the tensioning of the reinforced lung, drops in the filling pressure of the balloon may occur due to aspiration.

In contrast to a mechanical regulator 3 having a simple design, which provides an isobaric reserve volume of preferably 20 to 35 mbar, with the described electronic regulation a pressure may be built up which briefly exceeds the tracheal uncritical sealing pressure of 20 to 35 mbar, and may thus sealingly counteract pressure peaks in the tracheal balloon possibly caused by the patient.

Figure 9:
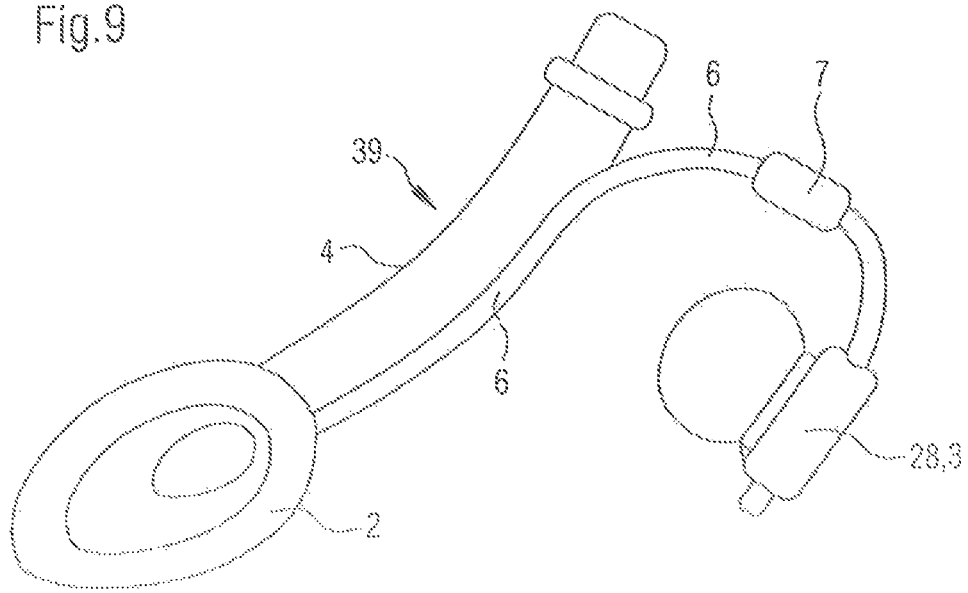
FIG. 9 shows a larynx mask with a connected regulator unit.

FIG. 9 shows a so-called larynx mask 39, which on a regulating reservoir unit 3 is equipped with flow-optimized feed lines 6, 9 as well as an optional valve-throttle combination 7 according to the invention. The closed balloon element 2, which is generally toroidal or ring-shaped, seals the larynx in the area of the hypopharynx, and is preferably made of a micro thin-walled PUR material corresponding to the materials proposed here for manufacturing the sealing balloon of tracheal ventilation catheters. For use in the hypopharynx, the regulator component is designed in such a way that a sealing pressure plateau DP of approximately 50 to 60 mbar develops within the communicating interior.

Figure 10:
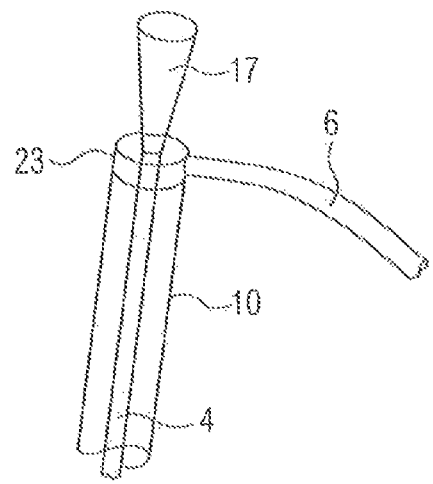
FIG. 10 shows a transesophageal probe with a connected regulator unit.
Figure 10:
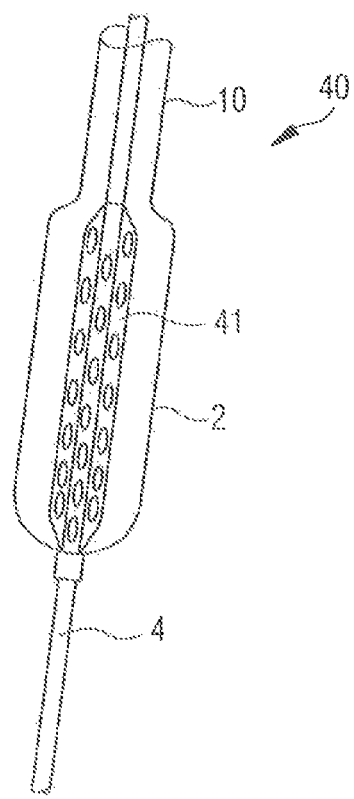

FIG. 10 shows a transesophageal probe 40 for supplying or discharging substances or media into the stomach or through the stomach, and which is equipped with an esophagus-sealing balloon element 2. The proximal balloon end 10 may be extended to the area of the extracorporeal connector 17. At this location it may be sealingly connected to a sealing closure element 23 that is freely movable on the shaft, and which in turn transitions into a large-bore feed line 6 that is connected to a regulation mechanism 3 according to the invention. For the esophageal sealing, the regulator component sets a sealing pressure plateau DP of approximately 20 to 30 mbar within the communicating interior.

To assist the tamponading sealing balloon segment in remaining stationary in the esophagus, the balloon segment may be provided with a noncollapsible profile 41 in the esophageal area, which, in the event of a peristaltic contraction of the esophagus, draws volume from the balloon segments in front of the peristaltic contraction, and through or underneath the profile in areas that have already been released from the contraction. Mushrooming of filling medium in front of the peristaltic contraction, which would result in transport of the entire device toward the stomach, may thus be prevented. Corresponding profiles have already been described in EP 0929339 B1, and within the scope of the present invention may be used to the full extent as disclosed therein.

The invention claimed is:

1. A device for the sealing occlusion and/or for the space-filling tamponade of a hollow organ or a cavity in a human body, comprising a fully and residually formed balloon (2) which is configured to apply an appreciably constant sealing pressure to a wall of the hollow organ or cavity to be occluded or tamponaded in use, characterized by an appreciably isobarically acting regulator for a filling pressure within the interior of the balloon (2), the regulator having an extracorporeal volume reservoir which is configured to be situated extracorporeally outside of the human body in use and a feed line (6) for communicatively connecting the extracorporeal volume reservoir of the regulator to the interior of the balloon (2), wherein the connecting feed line (6) between the balloon (2) and the regulator comprises:
   a) a supply channel with a cross-sectional area corresponding to a circular cross-sectional area with a diameter of at least 2 mm,
   b) a flow-directing one-way valve (26) that prevents backflow from the balloon (2) to the extracorporeal volume reservoir of the regulator, and
   c) a nonflow-directing throttle element (27) which allows a slow volume compensation between the balloon (2) and the extracorporeal volume reservoir,
   wherein the nonflow-directing throttle element (27) is arranged in parallel to the flow-directing one-way valve (26) as a bypass thereto.

2. The device according to claim 1, including a tube that is insertable into the hollow organ, with a primary lumen as access which is configured to be provided through or to the hollow organ or cavity in use, wherein the balloon has the shape of a cuff and encloses this tube for the purpose of sealing off with respect to the hollow organ or cavity, with at least one or multiple secondary lumen(s) for filling the balloon.

3. The device according to claim 2, characterized in that the balloon or a proximal area of the balloon ends at an end-face side of a hose-shaped element in which the primary lumen continues radially within a hose casing as a clear opening, while the at least one secondary lumen or the multiple secondary lumen(s) continues or continue in the form of one or more channels that are molded into the hose casing itself.

4. The device according to claim 3, characterized in that the minimum total cross section of all channels molded into the hose casing as the at least one secondary lumen or the multiple secondary lumens is greater than or equal to the maximum cross section of a ring-shaped secondary lumen in the proximal area of the balloon.

5. The device according to claim 2, characterized in that a ring-shaped collecting channel is present in the area of a proximal tube end, with which all channels of the secondary lumen communicate, in particular all channels that are molded into a hose casing as secondary lumens.

6. The device according to claim 5, characterized in that a connection for a filling hose that communicates with all secondary lumens is provided at the proximal tube end, in particular at the ring-shaped collecting channel.

7. The device according to claim 1, characterized by an apparatus for actively controlling or regulating the pressure in the extracorporeal volume reservoir.

8. The device according to claim 7, characterized in that the apparatus for actively controlling or regulating the pressure in the extracorporeal volume reservoir is designed in such a way that the pressure in the balloon (2) is held constant.

9. The device according to claim 8, characterized by an apparatus for measuring the pressure in the balloon (2), for the purpose of specifying an actual value for a control loop that acts on the pressure in the extracorporeal volume reservoir.

10. The device according to claim 2, characterized in that the balloon has a radially expanded distal area for sealing, and a proximal area adjacent thereto that is tapered radially with respect to same, as a covering of the secondary lumen(s) for filling the distal area.

11. The device according to claim 2, characterized in that a single secondary lumen is provided in a proximal area of the balloon which concentrically encloses the primary lumen on the outside.

12. The device according to claim 2, characterized in that a proximal area of the balloon does not extend to a proximal end of the tube, and instead ends prior to same.

13. The device according to claim 2, characterized in that the extracorporeal volume reservoir (9) in the freely unfolded state has a larger volume than the balloon (2), or has a larger volume than the balloon, in the distal area of the tube.

14. The device according to claim 1, characterized by a noncollapsible profile (41) inside the balloon (2) or inside a shaft which is configured to draw, in the event of a peristaltic contraction of the hollow organ, a portion of a filling medium from the balloon segments that are distal with respect to the contraction wave, preferably through the profile (41) or beneath the profile (41), in areas that are proximal with respect to the contraction wave.

15. The device according to claim 14, characterized in that the noncollapsible profile (41) communicates with the balloon (2) and/or its feed line and/or filling lumen of the balloon (2), in particular via one or more openings.

16. The device according to claim 1, characterized in that the balloon is pre-formed with different outer diameters in its distal and proximal areas.

17. The device according to claim 1, characterized in that a radially tapered area which is configured for the glottis in use is molded into the balloon or into a distal area of the balloon.

18. The device according to claim 1, characterized in that the extracorporeal volume reservoir (9) is acted on with a constant pressure or an appreciably constant pressure, for example by a weight or a spring element.

19. The device according to claim 1, characterized in that the balloon (2) is closed in a ring shape, and in particular has a toroidal design.

20. The device according to claim 1, characterized in that the balloon (2) is designed as a larynx mask, in particular for placing on the hypopharynx.

21. The device according to claim 1, characterized in that the flow-directing one-way valve (26) and/or the nonflow-directing throttle element (27) are/is extracorporeally situated.

22. A device for the sealing occlusion and/or for the space-filling tamponade of a hollow organ or a cavity in a human body, comprising a prefcrably fully and residually formed balloon (2) which is intended to be configured to apply an appreciably constant sealing pressure to a wall of the hollow organ or cavity to be occluded or tamponaded in use, comprising a regulating unit for a filling pressure within the interior of the balloon (2), which regulating unit is intended to be configured to be situated extracorporeally outside of the human body during use and comprises an extracorporeal volume reservoir (9) which is intended to be configured to be situated extracorporeally outside of the human body in use, and a feed line (6) for communicatively connecting the extracorporeal volume reservoir (9) to the interior of the balloon (2), wherein the connecting feed line (6) between the balloon (2) and the extracorporeal volume reservoir (9) comprises (i) a supply channel with a cross-sectional area corresponding to a circular cross-sectional area with a diameter of at least 2 mm, (ii) a flow-directing one-way valve (26) that prevents backflow from the balloon (2) to the extracorporeal volume reservoir (9), and (iii) a nonflow-directing bypass throttle element (27) which allows a slow volume compensation between the balloon (2) and the extracorporeal volume reservoir (9), wherein the nonflow-directing throttle element (27) is arranged in parallel to the flow-directing one-way valve (26) as a bypass thereto, and wherein the regulating unit is implemented
   a) as a combined regulator and volume reservoir unit (3), where the extracorporeal volume reservoir (9) comprises a volume-expandable balloon bladder (28) made of a material with an elasticity sufficient to increase the volume due to an increasing pressure in order to provide a constant pressure or an appreciably constant pressure inside the extracorporeal volume reservoir (9), or
   b) as a weight or a spring element acting on the extracorporeal volume reservoir (9) with a constant pressure or an appreciably constant pressure.

23. A device for the sealing occlusion and/or for the space-filling tamponade of a hollow organ or a cavity in a human body, comprising a preferably fully and residually formed balloon (2) which is intended to be configured to apply an appreciably constant sealing pressure to a wall of the hollow organ or cavity to be occluded or tamponaded in use, comprising a regulating unit for a filling pressure within the interior of the balloon (2), which regulating unit is intended to be configured to be situated extracorporeally outside of the human body in use and comprises an extracorporeal volume reservoir (9) which is intended to be configured to be situated extracorporeally outside of the human body in use, and a feed line (6) for communicatively connecting the extracorporeal regulating unit to the interior of the balloon (2), wherein the connecting feed line (6) between the balloon (2) and the extracorporeal volume reservoir (9) comprises:
   a) a supply channel with a cross-sectional area corresponding to a circular cross-sectional area with a diameter of at least 2 mm,
   b) a flow-directing one-way valve (26) that prevents backflow from the balloon (2) to the extracorporeal volume reservoir of the regulator,
   c) a nonflow-directing throttle element (27) which allows a slow volume compensation between the balloon (2) and the extracorporeal volume reservoir,
   d) wherein the nonflow-directing throttle element (27) is arranged in parallel to the flow-directing one-way valve (26) as a bypass thereto, and wherein the regulating unit comprises:
   e) either a control apparatus for actively controlling the pressure in the extracorporeal volume reservoir (9) which is designed in such a way that the pressure in the balloon (2) is held constant, or
   f) a regulating apparatus for actively regulating the pressure in the extracorporeal volume reservoir (9) as a result of the pressure measured in the balloon (2) by a measuring sensor arranged inside of the balloon (2) for the purpose of specifying an actual value for a control loop that acts on the pressure in the extracorporeal volume reservoir (9).

\* \* \* \* \*